(12) United States Patent
Tavares (10) Patent No.: US 9,554,261 B1
(45) Date of Patent: Jan. 24, 2017

(54) RESPONDING TO A MESSAGE GENERATED BY AN EVENT NOTIFICATION SYSTEM

(71) Applicant: David Tavares, Kleinburg (CA)

(72) Inventor: David Tavares, Kleinburg (CA)

(73) Assignee: Globestar, Inc., Toronto (CA)

( * ) Notice: Subject to any disclaimer, the term of this patent is extended or adjusted under 35 U.S.C. 154(b) by 0 days.

(21) Appl. No.: 14/800,831

(22) Filed: Jul. 16, 2015

(51) Int. Cl.
*H04M 11/04* (2006.01)
*H04W 4/22* (2009.01)
*H04W 4/12* (2009.01)
*H04M 1/725* (2006.01)

(52) U.S. Cl.
CPC ........... *H04W 4/22* (2013.01); *H04M 1/72538* (2013.01); *H04W 4/12* (2013.01)

(58) Field of Classification Search
USPC ....................... 455/414.1, 404.1, 567, 456.1, 456.3, 455/414.2, 418
See application file for complete search history.

(56) References Cited

U.S. PATENT DOCUMENTS

| | | | | |
|---|---|---|---|---|
| 8,825,043 | B2* | 9/2014 | Rogalski | H04M 1/2725 455/404.1 |
| 9,349,366 | B2* | 5/2016 | Giancarlo et al. | G10L 15/04 |
| 2011/0029875 | A1* | 2/2011 | Milch | B60R 25/104 715/727 |
| 2013/0070928 | A1* | 3/2013 | Ellis | H04R 25/30 381/56 |
| 2013/0084923 | A1* | 4/2013 | Schuman | H04W 4/00 455/567 |

* cited by examiner

*Primary Examiner* — David Q Nguyen
(74) *Attorney, Agent, or Firm* — Robert Schuler (57) ABSTRACT

A mobile communication device (FOB) attached to a user operates on sound information utter by the user to respond to alert messages sent to it by an event notification system (ENS). The FOB is able to transition between a training mode and a normal mode of operation. In the training mode of operation, the FOB can detect and store sound information associated with a user's response to a training alert message. The sound information in the user response to the training alert message is associated with a response code that the user is prompted to enter into the FOB during the training process. In the normal mode of operation, the user can respond to an alert message played by the FOB with a verbal utterance, and the FOB generates and sends a response message to the ENS that includes the response code associated with the training verbal response.

19 Claims, 9 Drawing Sheets

FIG. 8A — NORMAL OPERATING MODE LOGIC

FIG. 8B

RESPONDING TO A MESSAGE GENERATED BY AN EVENT NOTIFICATION SYSTEM

1. FIELD OF THE INVENTION

The present disclosure relates to an event notification system and method for training a communication badge to respond to an event notification system alert message.

2. BACKGROUND

An event notification system (ENS) can operate in many different types of environments to receive messages, from a variety of input devices and systems, that have information about many different types of events, they can operate to determine how to react to information received in the messages and to generate and send an alert message to one or more individuals, and they can operate to receive and process responses to the alert messages. An ENS can be configured to operate in a number of different environments, such as a financial environment, emergency service environment, manufacturing environment, in healthcare environment and in many other types of environments. When operating in a healthcare environment, an ENS can receive event information in a message generated by a patient monitor, it can receive a message generated at a call point (CP) for supplies or for patient transport, and it can receive messages generated by a nurse, doctor or other healthcare staff or systems relating to patient care. Regardless of the origin of an event message, the ENS can operate to determine the origin of an event message and it can determine whether or not to take further action with respect to the message. In the event that the ENS sends an event message to an individual and receives a response, the ENS operates to determine whether information in the response requires any further action.

Figure 1A:
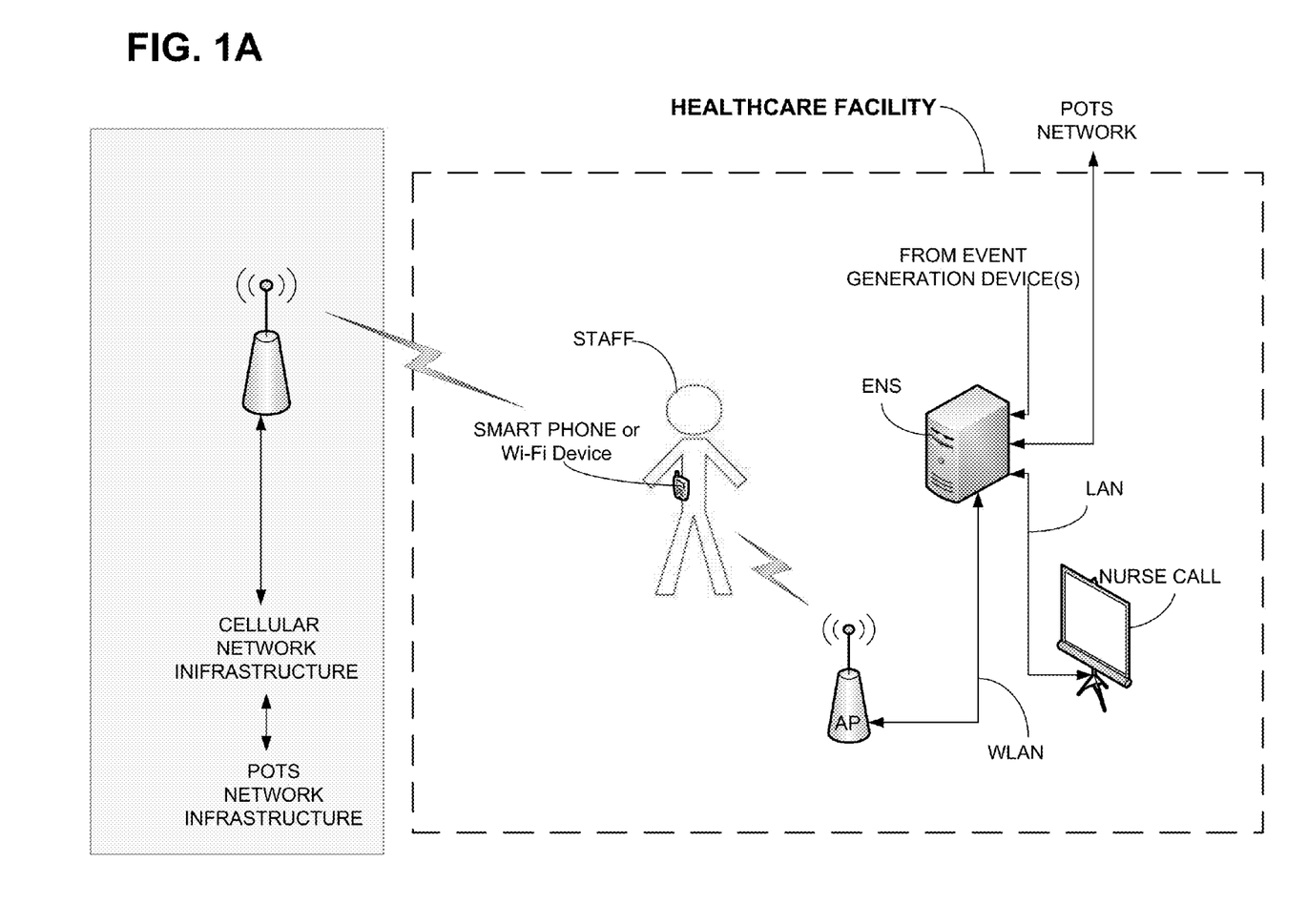
FIG. 1A is a diagram illustrating a wireless communication network in a healthcare facility connected to an event notification system.

Event notification systems can be configured to link with wireless networks and to send and receive alert messages to and from mobile communication devices (i.e., wireless communication badge, smart phone or Wi-Fi phones). When configured to communicate over a wireless network, it is not necessary for medical staff to be paged, and then have to locate the closest wired communication device (i.e., POTS phone) in order to respond to an alert message. Instead, staff can use their mobile device to immediately respond to an alert message regardless of their location, and provided their mobile communication device is within range of a wireless network. This wireless notification and response capability has improved medical staff response time to patient emergencies and generally improved the efficiency and patient satisfaction with which staff is able to work in a healthcare environment. FIG. 1A shows an event notification system (ENS), located in a healthcare facility, that is configured to connect with two types of wireless networks (Cellular & Wi-Fi), and a wired (POTS) communication network. The ENS operates to send alert messages over either the Wi-Fi or Cellular network to a mobile communication device associated with a healthcare staff member, and it operates to receive alert message responses from the mobile device. The ENS is also connected to a plurality of event generation devices such as patient monitors and to call points. The patient monitors operate to detect physiological information relating to a patient and send this information to the ENS, and the call points are positioned strategically throughout the healthcare facility to serve as an ENS communication portal for the staff.

3. BRIEF DESCRIPTION OF THE DRAWINGS

The present invention can be best understood by reading the specification with reference to the following figures, in which.

4. DETAILED DESCRIPTION

While event notification systems can be configured to send and receive alert messages (voice or text alert messages) to mobile devices, most mobile devices require that a user handle the device in order to generate a response to an alert message, or if the mobile device can recognize verbal commands, a verbal response to an alert message needs to be converted to textual information at the mobile device or at an ENS before the ENS can use the information in the response to determine if any action should be taken, such as escalating the response by sending the same alert to another staff member. Further, the text information in the alert response message received by the ENS has to be analyzed before the ENS is able to determine if it should initiate any further action(s). In this regard, the ENS can employ key word matching methods to determine the meaning of a response. So for instance, if an alert message prompts a mobile device user to respond by acknowledging the alert, the user can utter a response (i.e., ACKNOWLEDGE/YES/NO), then functionality in either the mobile device or the ENS can convert the verbal response information to text response information, and functionality in the ENS can operate on the text information in the response to determine what the text information means. After the ENS understands the meaning of the response, it can then determine whether it should initiate an action(s) or not. While the ability to respond to an ENS alert message verbally is very convenient for healthcare staff, it requires that additional functionality (speech to text conversion and text recognition) is implemented in a mobile communication device and/or in the ENS. This additional functionality adds cost and complexity to the mobile device and ENS and the response back from the mobile device may occupy a voice channel.

In order to lower the cost and complexity of both a mobile communication device and an ENS with which the mobile device can communicate, it was discovered that a mobile communication device can be placed into a training mode of operation (alert message response training operation), and while in this training mode a verbal or other type of response to an alert training message can be associated with an assigned alert message response code. Then, when in a normal mode of operation, the mobile communication device can receive an alert message from the ENS, a mobile device user can respond to the alert message with an utterance or some other type of sound (audible or inaudible) which can be associated with the alert message response code, and the alert message response code can be sent over a data channel to the ENS. Utilizing such a training method obviates the need for the more complex and costly voice to text conversion process normally employed. This simple training process can be implemented in a mobile communication device that has a mode selection switch that a user can actuate to select either a training mode of operation or a normal mode of operation. In the training mode, the mobile device user can utter one or more words or sounds (or come combination of both) into the mobile device, in response to a training/sample alert message, and then assign a code to the response by depress a mode selection switch one or more times. Alternatively, the response code can be assigned without depressing the mode selection switch, and the code can be assigned verbally or in some other manner. Functionality in the mobile device, or an ENS with which the mobile device is able to communicate, associates the utterance with the number of times the mode switch is depressed, and stores this association as an alert response code for use during the normal operating mode. When in the normal operating mode, the mobile device user can respond to a voice alert message from the ENS by uttering a response that the mobile device detects and converts to the associated alert response code (i.e., digital code) and sends to the ENS in an alert response message. The ENS matches the alert response code to a response type and determines whether or not any action should be taken.

Figure 1B:
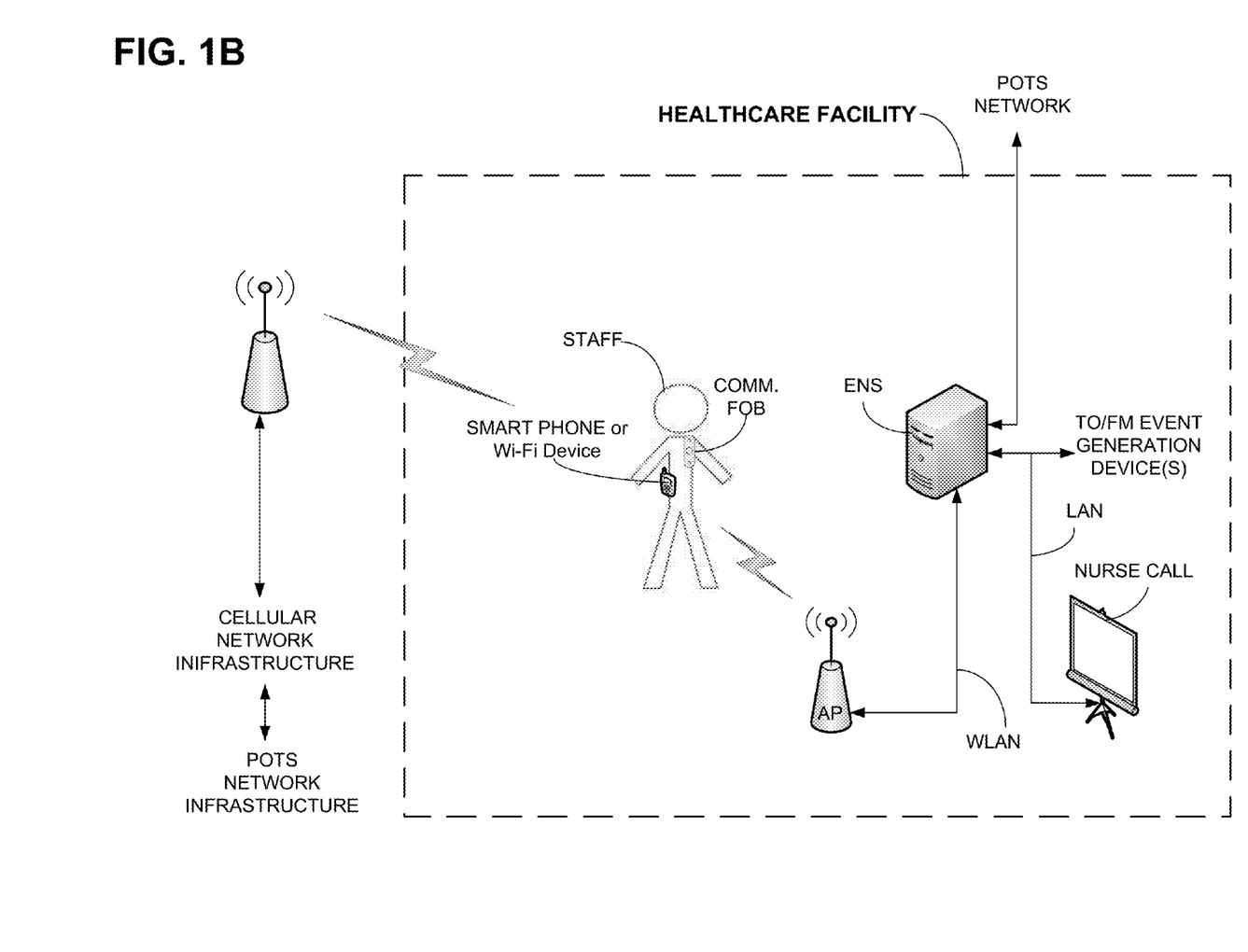
FIG. 1B is a diagram that is similar to FIG. 1A with the addition of a communication FOB.

In one embodiment, the alert message response training operation can be entirely supported by functionality implemented in a mobile communication device, and in another embodiment, support for the response training operation can be shared between the mobile device and the ENS. For the purpose of this description, the operation of the alert message response training functionality is supported entirely in a mobile communication device. In this regard, FIG. 1B shows one embodiment of a mobile communication device that is worn by a healthcare staff member and labeled as a communication FOB. The communication FOB, or simply FOB, is configured to communicate over a wireless LAN (Wi-Fi for instance) with an event notification system (ENS), which in turn is configured to receive information over a LAN from various types of event generation devices or systems (patient monitors, ventilators, nurse call station, etc.). Generally, an event generation device, such as a patient monitor, can send patient physiological information to the ENS, and the ENS can use this information to determine what information should be included in an alert message, and to whom/who the alert message should be sent. The ENS can generate and send the alert message to a mobile communication device, such as the FOB, that is currently associated with a particular staff member. Subsequent to a training procedure, the staff member can respond to the alert message with an utterance (a recognizable word or a sound not recognizable as a word) that is detected by the FOB, and the FOB can then compare the utterance with a plurality of instances of utterances created during the training procedure and stored in the FOB looking for a match. Each stored instance of an utterance is associated, during the training process, with a response code, and this response code is included in a response message that the FOB can send to the ENS. Depending upon the alert message response code received from the FOB, the ENS can initiate an action, such as to cancel or delay the alert, escalate the alert, send a message that a task is completed, request supervisory involvement, request a call back, request that the task be transferred to another, or initiate some other action. The functionality comprising the FOB will be described below with reference to FIG. 2.

Figure 2:
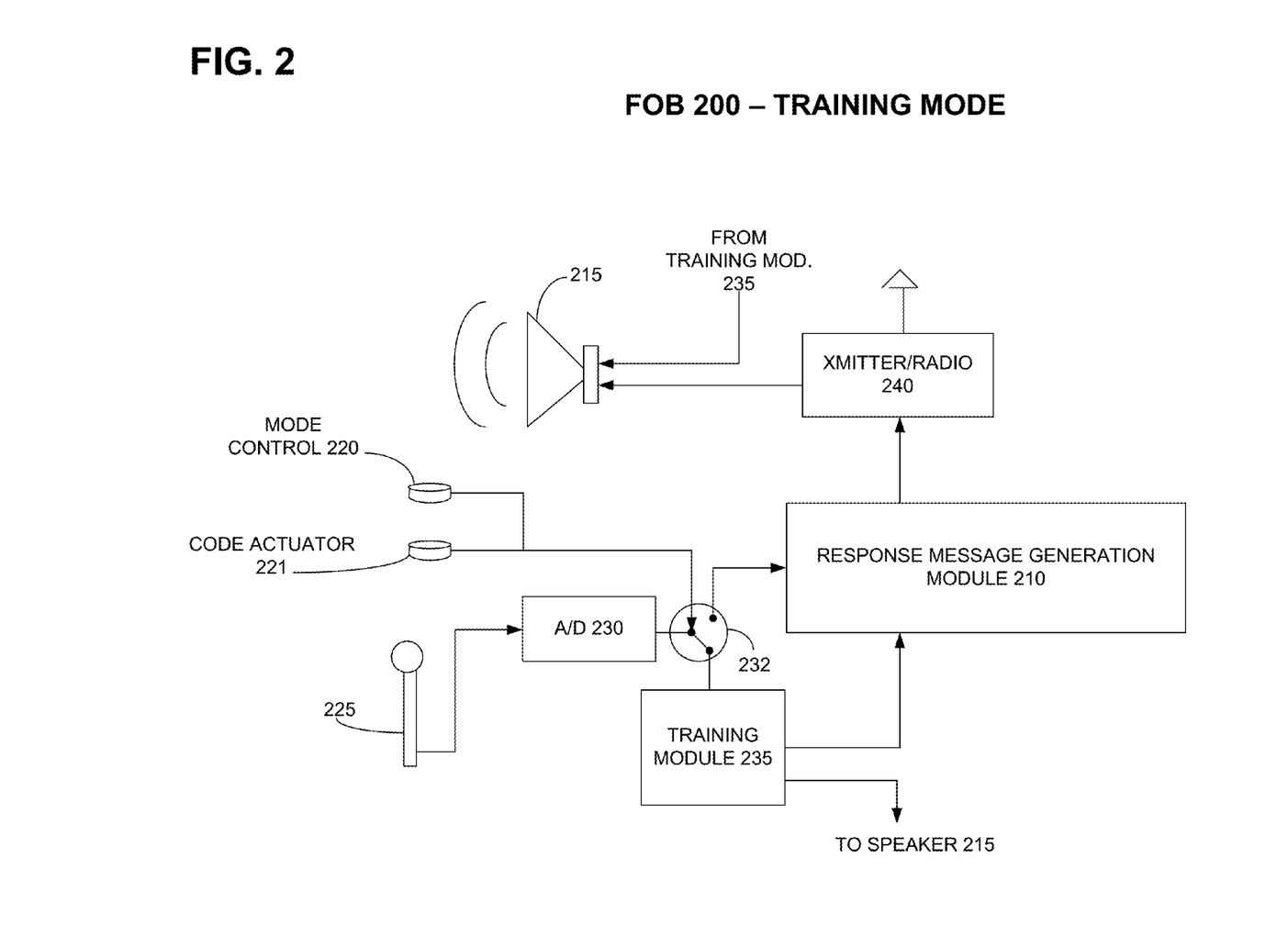
FIG. 2 is a block diagram illustrating functional elements comprising a mobile communication device 200 operating in a training mode.

FIG. 2 shows functional elements comprising a mobile/wireless communication device or FOB 200 that is in a training mode of operation. The FOB 200 has a response message generation module 210 to which is connected a radio transceiver 240, and a training module 235. The functional elements comprising the FOB 200 can rely upon power from a rechargeable battery (not shown), and the FOB can be connected with a charging dock when not in use in order to recharge the battery. The message generation module 210 operates to maintain store of training utterances and associated response codes, it operates to detect and temporarily store user utterances for at least as long as it take to compare the utterance to one or more stored instances of training utterances, and the module 210 operates to format a response message to include a response code (and possibly other information) and to send the formatted response message to the radio 240 for transmission to an ENS. The radio operates to receive alert messages from the ENS, and to send them to the speaker 215 where they are played. The alert messages can have audio information that when played by the FOB serve to inform the user that an action should be taken. This action can be to respond to an event generated by a patient monitor or an event generated by a staff member, or an event generated in some other manner. The FOB 200 has a microphone 225 that operates to receive audio information from the environment, and particularly to receive sounds in the form of an utterance from the FOB user. The utterance is passed to an analog to digital converter (A/D) 230, and the resulting digitized audio information is, in the training mode, passed to the training module 235. The FOB also has a mode control selection mechanism that is comprised of an actuator 220 that controls the position of a switch 232. The actuator 220 can be manipulated by the FOB user to control the position of the switch 232 in order to select the mode of the FOB operation. When in the training mode, a code actuator 221 can be manipulated by the FOB user to assign a response code to an utterance.

Continuing to refer to FIG. 2, during the training mode of operation, a training alert message, stored at the FOB or ENS, can be played by the FOB 200, and the FOB user can respond to the training message with an utterance (training utterance) and immediately thereafter press the code actuator 221 one or more times. The sound associated with the training utterance is stored with the assigned response code either at the FOB or it is sent by the FOB to the ENS for storage and to be used during a normal FOB mode of operation. Alternatively, the code actuator 221 can be pressed immediately prior to the user responding to the training alert message with the utterance. Each training alert message is assigned one or more valid training utterances. For instance, a training alert message "Please attend to patient in room # X", can have several valid responses, each one or which is assigned a different response code to the mobile device user. One training utterance can be "ACKNOWLEDGE ALERT AND NOT BUSY", OR "ACKNOWLEDGE ALERT BUT BUSY", OR "ACKNOWLEDGE ALERT & REQUEST ASSISTANCE". Each of these training utterances can be assigned a different code by the user. In this regard, the training utterance "ACKNOWLEDGE ALERT AND NOT BUSY" can be assigned the response code "1" by the user, and so forth for the other possible utterances.

As described above, the operational mode of the FOB 200 is determined by the position of the switch 232 that is connected to the output of the A/D converter 230 and which is connected to the inputs of the message generation module 210 and the training module 235. In FIG. 2, the position of the switch connects the output of the A/D converter 230 to the training module 235, and so the FOB 200 is in the training mode of operation. In this mode, the FOB is not enabled to receive alert messages from the ENS, but is able to play one or more instances of a training alert message stored in memory associated with the FOB or stored in memory associated with the ENS.

Figure 3:
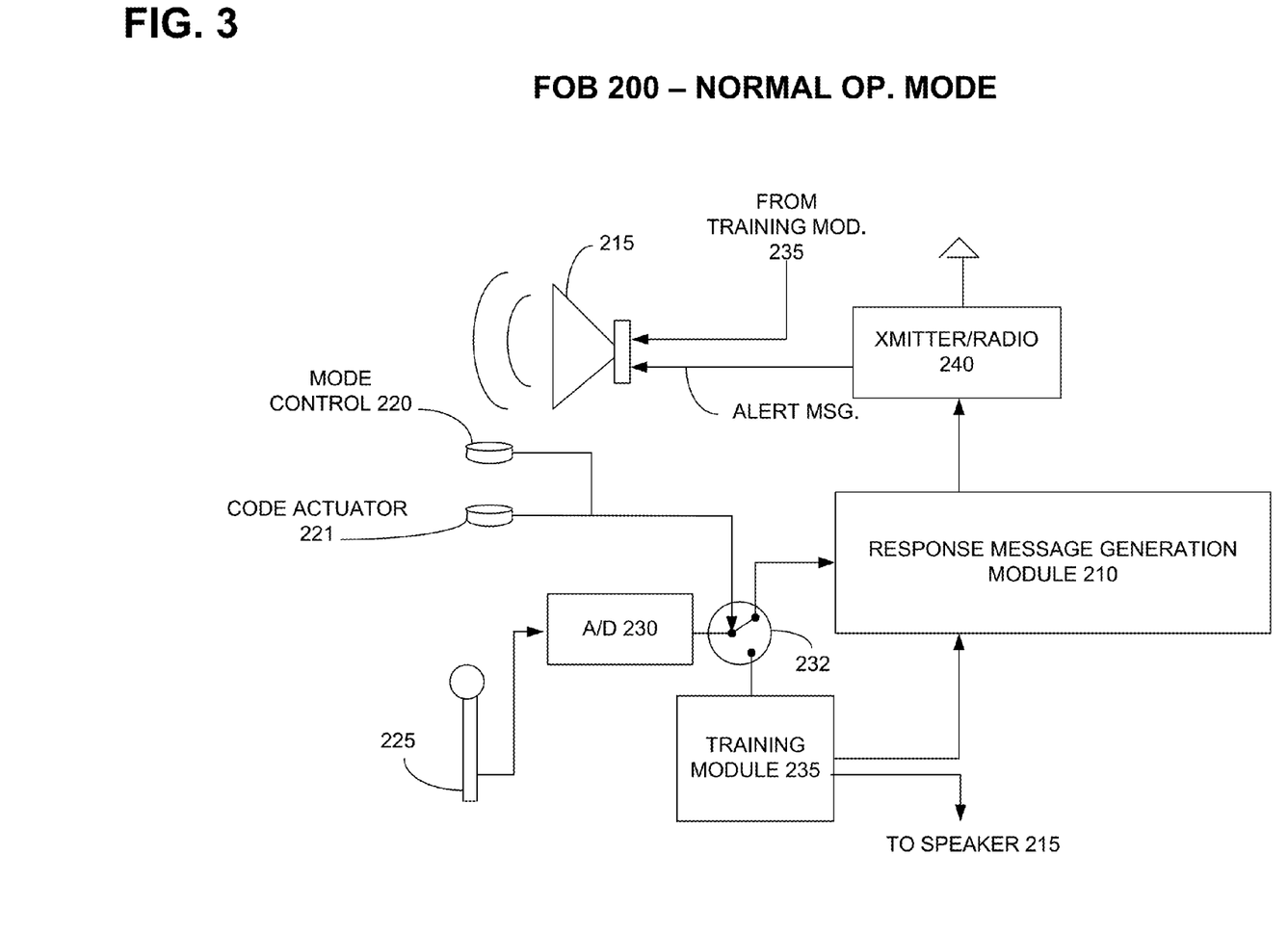
FIG. 3 is a block diagram illustrating functional elements comprising a mobile communication device 200 in a normal operating mode.

FIG. 3 shows the same FOB 200 as described earlier with reference to FIG. 2, with the exception that the switch 232 position shows the FOB to be in the normal mode of operation in which the path of the digitized audio signal runs from the A/D converter 230 through the switch 232 to the response message generation module 210. In this mode of operation, the FOB is enabled to receive alert messages from the ENS, and the FOB user can respond to the alert message from the FOB. The FOB can send a digitized version of the alert response utterance to the response message generation module 210, where sound information in the utterance is matched to sound information comprising an instance of a stored, training utterance. When a match is detected between the alert response utterance and a stored, training utterance, the response code that is stored in association with the matching training utterance is placed into an alert response message and transmitted by the radio 240 to the ENS.

Figure 4:
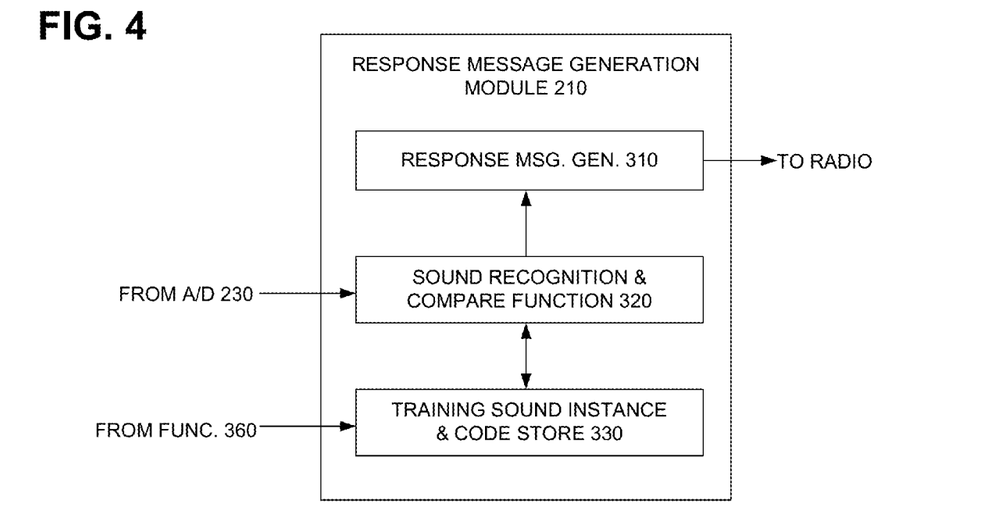
FIG. 4 is a block diagram showing functional elements in a response message generation module 210 comprising the mobile communication device 200.

FIG. 4 shows the functional elements comprising the response message generation module 210 of FIGS. 2 and 3 in more detail. The response message generation module 210 shown in FIG. 4 has a response message generator 310, a sound recognition, a compare function 320, and a training sound instance and code store 330. The store 330 receives and maintains a plurality of instances of training sound information from the training module and the response code assigned to each. The sound recognition and compare function 320 receives and temporarily stores sound information comprising an alert response message from the A/D converter 230, and it operates on this sound information in the alert response message and sound information in the store 330 to find an instance of sound information in the store 330 that matches the sound information in the alert response message. When a match is detected, the associated response code is passed to the response message generator which includes the code in a formatted response message that the radio transmits to the ENS.

Figure 5:
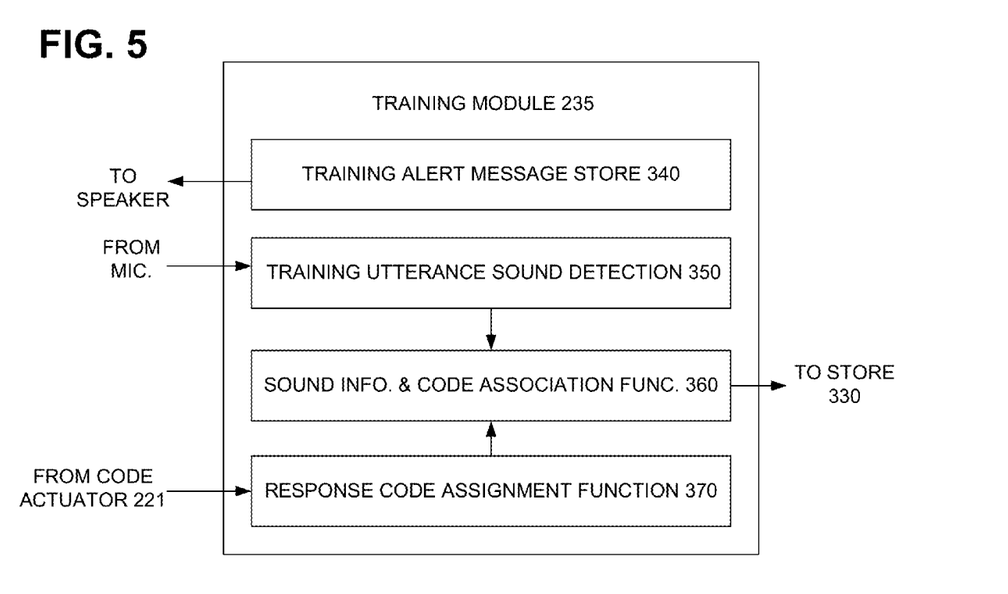
FIG. 5 is a block diagram showing functional elements in a training module 235 comprising the mobile communications device 200.

FIG. 5 show the functional elements comprising the training module 235 of FIGS. 2 and 3 in more detail. Training module 235 has a store of training alert messages 340. The messages stored here can be loaded into the FOB and periodically updated as necessary whenever the FOB is powered and connected to the WLAN described with reference to FIG. 1A. As will be described later with reference to FIG. 6, a current store of training alert messages can be maintained in the ENS and periodically published to all FOBs then connected to the network. Each training alert message can be comprised of one or more audible words and/or numbers and an audible instruction to assign a particular response code to the user's response. When the FOB is placed into the training mode by the FOB user, at least one training alert message can be played, next the response code instruction can be played, after which the user can utter a response. Alternatively, the training alert message is played after which the user utters a response, and then the user is instructed to enter a response code (by pressing the code actuator 221 one or more times as instructed, for instance). The training alert response message is received by a training utterance sound detection function 350 which operates to detect sound information in the response message. The function 350 can create a sound fingerprint from the sound information in the response message. This sound fingerprint can represent audible sound spectrum information over the period of time during which the response message is detected. This instance of a sound fingerprint is passed to a sound information and code association function 360 where it can be stored for as long as necessary.

Continuing to refer to FIG. 5, a response code assignment function 370 receives code information from the code actuator 221 each time the FOB user depresses (for example) the actuator. Each time the actuator is depressed it generates an electrical signal, and while the FOB is in the training mode, the function 370 receives this electrical signal and can interpret it as a binary 1, for instance. Depending upon coding instructions included in the training alert message, the user can depress the actuator 221 once or multiple times immediately prior to or after uttering a response to the training alert message, and the function 370 can pass the code entered by the user to the sound information and code association function 360. The function 360 associates the response code information with the just received instance of sound information (or vice versa), and sends it to the training sound instance and code store 330 in the response message generation module 210. After all of the training alert messages are played, and after a FOB user utters a responses to each training message and assigns a code to each training message response, the FOB is fully operational and can be used to respond to any alert message sent to it by the ENS. When in the normal operating mode, a FOB user can respond to an alert message by merely vocalizing a response without having to physically touch or manipulate any part of the FOB. The response message carries all of the information need for the ENS to determine whether or not to cancel the alert, to escalate the alert, or to send another alert message to the same FOB.

Figure 6:
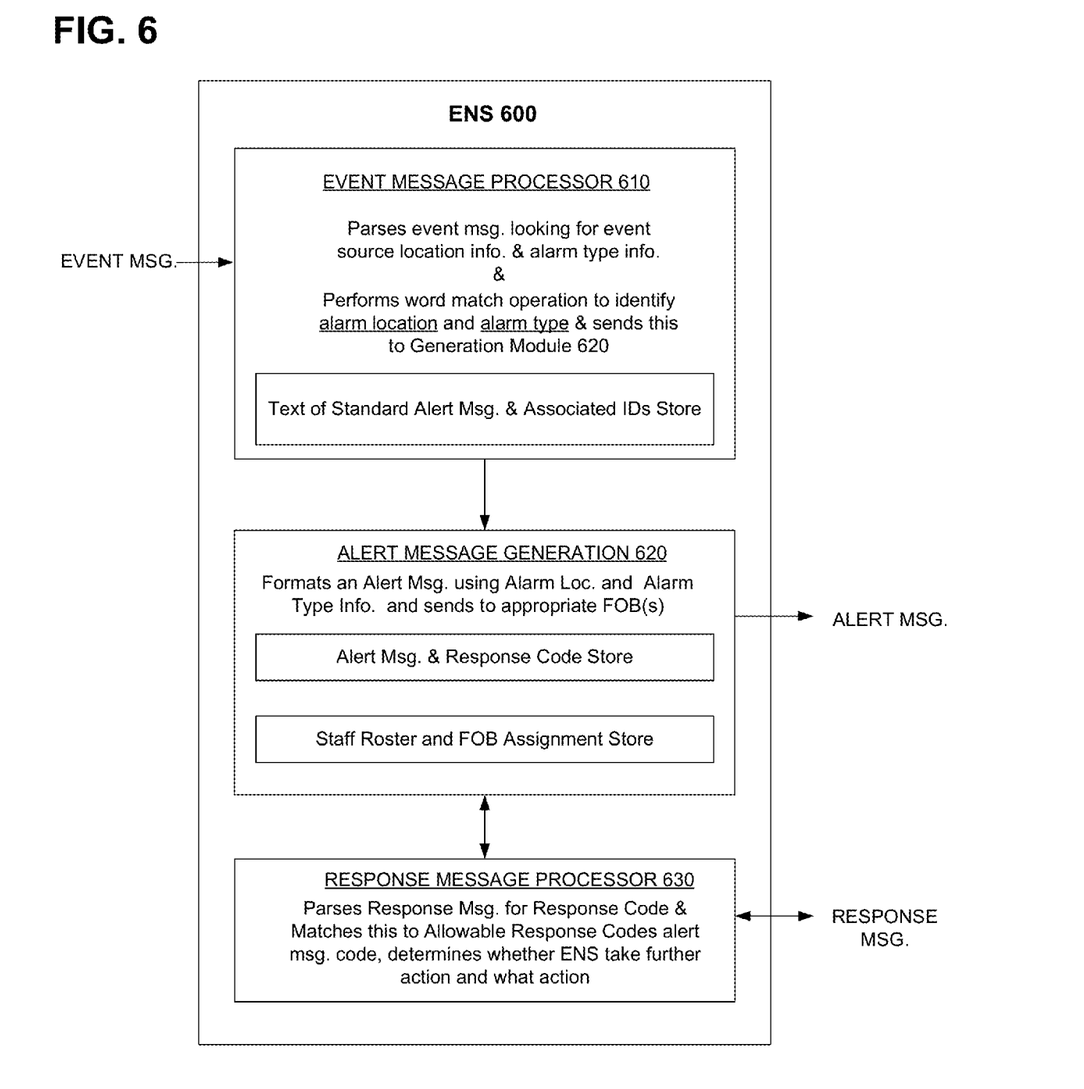
FIG. 6 is a high level block diagram illustrating functional elements comprising an event notification system (ENS) 600.

FIG. 6 represents a high level block diagram of an ENS 600 that generally operates to receive event messages from event generation devices and/or other systems connected to the healthcare LAN, to generate and send alert message to one or more appropriate individuals, and to receive and process responses to the alert messages. The ENS 600 has an Event Message Processor 610, and Alert Message Generation module 620 and a Response Message Processor 630. The Event Message Processor 610 operates to receive event message information from event message generation devices, and to parse the event message looking information relating to the source of an event message (particular geographic location such as a room number), and looking for information relating to the type of alert. An event message is formatted such that the position (bit numbers(s)) of the event location, event type and additional relevant event information is known by the ENS 600. This allows the ENS to parse each event message and identify information relating to location information and event type information.

Information relating to an event location can be a unit and a room number. The unit can be an emergency room (ER) unit, a cardiac (CA) unit or any other type of unit located in a healthcare setting, and the room number information can include a number and a letter, such as 412A. The event type information can include such things as heart rate (HR) information, respiratory rate (RR) information, blood pressure (BP) information, or any other monitored patient physiological alarm information.

After the event source location information and the event type information are detected, the processor 610 can perform a key character (alphanumeric) type matching operation during which the detected alphanumeric location and event type information are compared to alphanumeric characters in a plurality of standard alert message stored in association with the processor 610. The ENS is able to identify which one of a plurality of event messages to send when there is a match between the information in the event message and information in a standard alert message, and the processor can send the identity of the alert message and the event location and type information to the Alert Message Generation module 620.

The module 620 uses information in a staff roster (identity of an individual or individuals currently on duty and who are responsible for particular type of events in particular locations, the network address of a FOB assigned to this/these individuals areas) to identify one or more individuals who should receive the alert message. The generator then formats the identified alert message with the event location and event type information, sends the alert message to the appropriate staff, and sends a message to the Response Message Processor 630 that has information indicating what type of event message was sent, indicating what valid response codes to expect, and indicating to which individual(s) the event message is sent and when.

With continued reference to FIG. 6, the Response Message Processor 630 can receive an alert response message from one of more FOBs that has a response code. It examines the response message for a response code, and if it detects a valid response code, it uses this code to determine whether to cancel the alert, escalate the alert, to send another alert to the same FOBs, or to take any other action.

The operational control of a FOB, such as the FOB 200 described with reference to FIG. 2 and FIG. 3, can be implemented in logical instructions maintained in non-volatile memory in the FOB. These logical instructions can be designed to control the transition of the operational mode of the FOB between a training mode and a normal mode. The logic controlling the FOB while in the training mode will now be described below with reference to FIG. 7.

Figure 7:
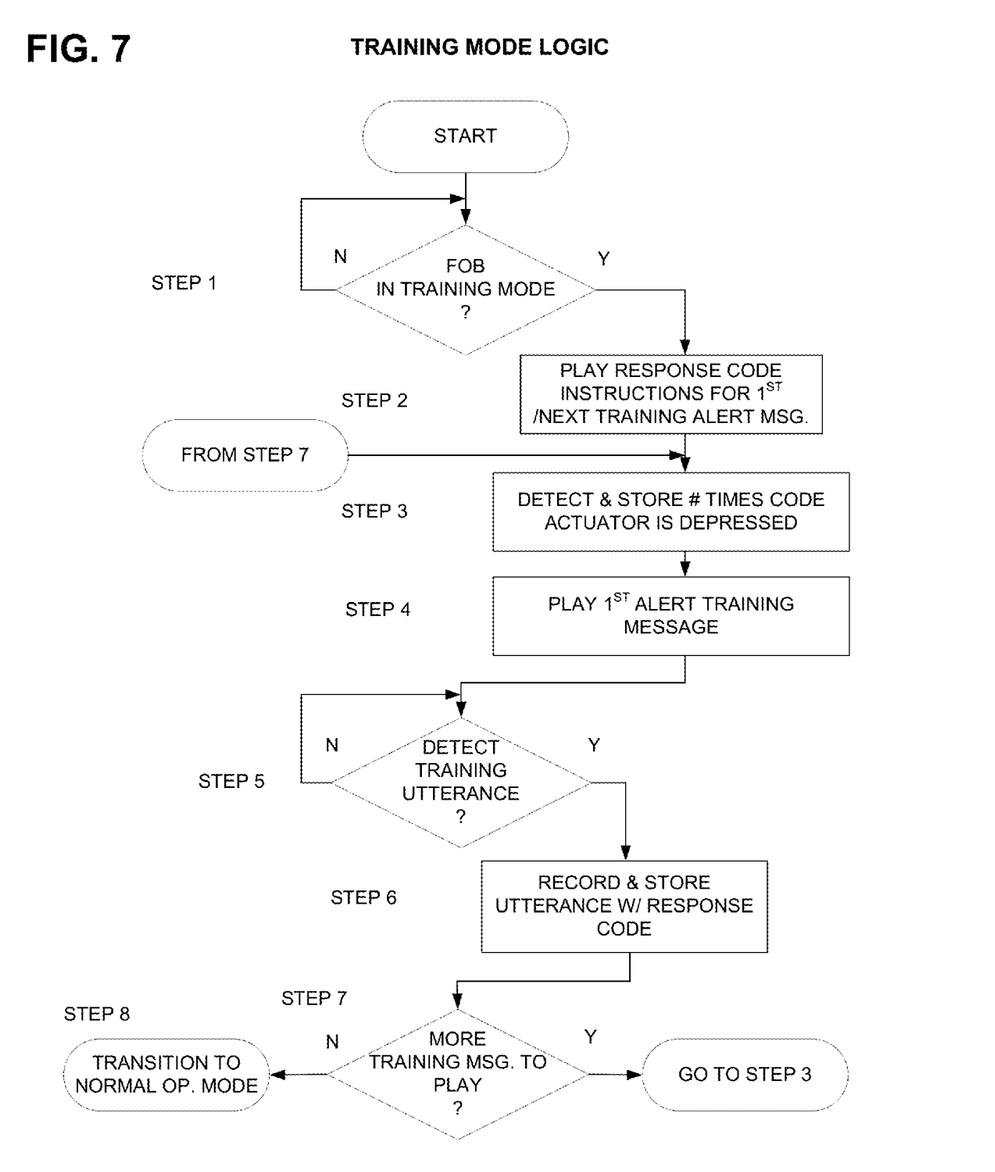
FIG. 7 is a logic diagram showing the operation of training logic operating in the mobile communication device 200.

Subsequent to the FOB 200 being activated or powered up, in Step 1 of FIG. 7 the FOB can be placed into the training mode by the FOB user by depressing the module control switch 220 or by uttering a verbal command. Once the FOB is in the training mode of operation, the process proceeds to Step 2 and instructions, corresponding to a first training alert message, to depress the code actuator button one or more times are played from the store 340 maintained in the training module 235. In Step 3, the logic detects and stores in the code store 330 a code representing the number of times the user depresses the code actuator button 221, and the first alert training message (maintained in the store 330) is played in Step 4. If in Step 5 the sound recognition function 330 detects a response utterance, then the process proceeds to Step 6, otherwise the process loops on Step 5 waiting for a response utterance from the FOB user. If no response utterance is detected the process can time out after a selected period of time. In Step 6, the sound information comprising the response utterance is stored in the training sound instance store 330 in association with the response code stored in Step 3 and the process proceeds to Step 7. In Step 7 the logic determines whether or not there are any more training messages to play, and if so, the process returns to Step 3, otherwise the logic controls the FOB to transition to the normal operational mode in Step 8.

Typically, when not in use, the FOB can be stored in a docking/charging station. When coming into contact with the docking station, the FOB can transition to a standby mode of operation in which it is not able to receive alert messages.

Figure 8A:
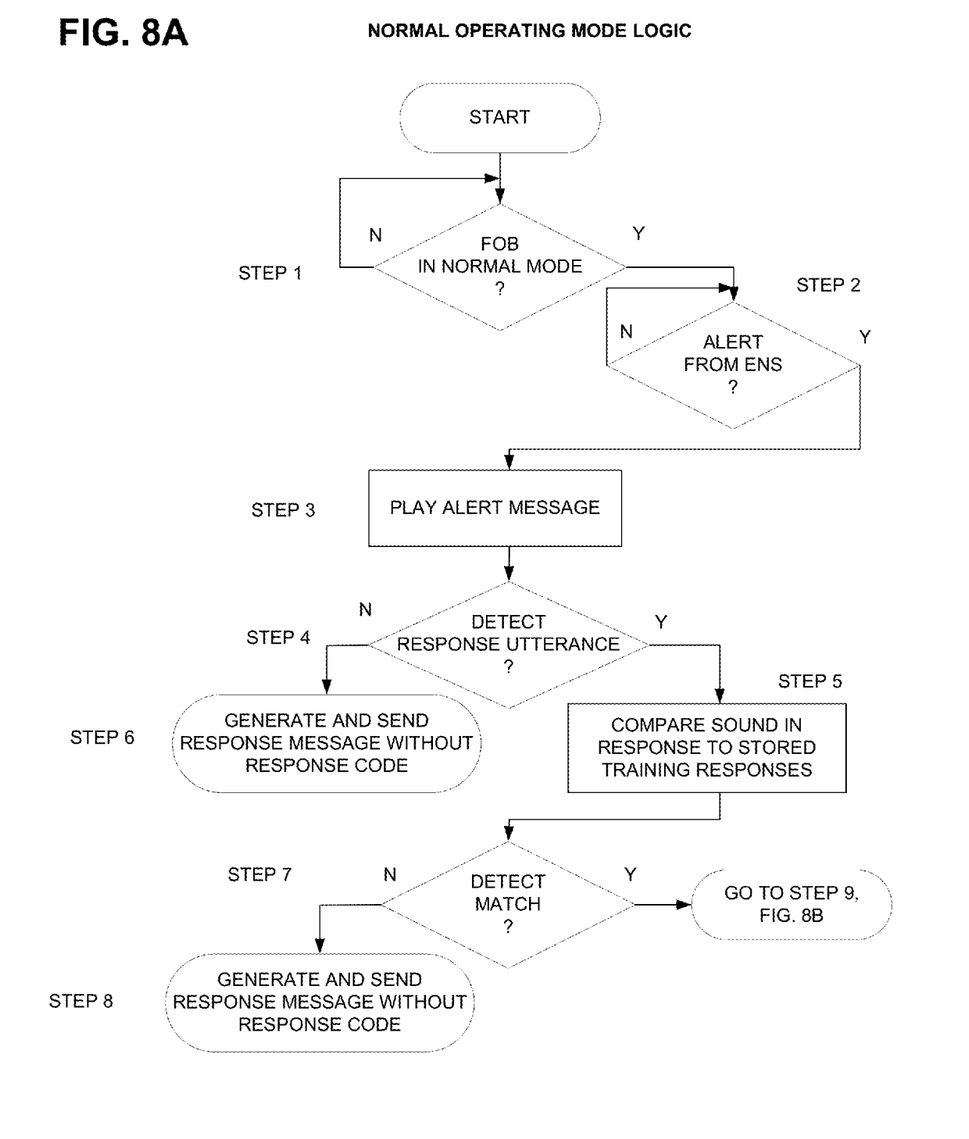
FIG. 8A is a logic diagram showing the wireless communication device 200 operating in a normal mode.
Figure 8B:
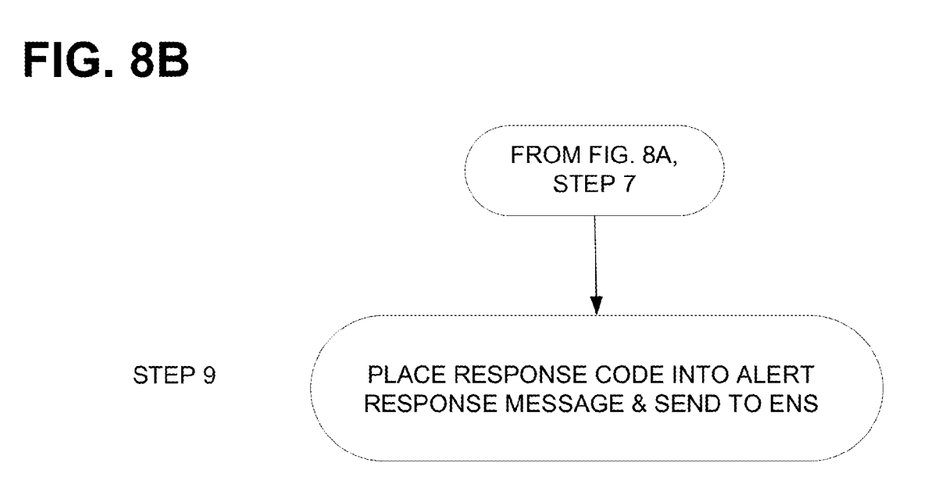
FIG. 8B is a continuation of the logic diagram in FIG. 8A.

The logic controlling the normal operational mode of the FOB will now be describe with reference to FIGS. 8A and 8B. After the FOB is removed from the charge dock, it can be controlled by the logic, in Step 1, to transition to the normal mode of operation. After transitioning to the normal operational mode, the FOB is enabled to receive alert message sent to it by the ENS 200. The process loops on Step 2 until the FOB receives an alert message, at which point the process proceeds to Step 3 and the alert message is played on the FOB speaker. In Step 4, if the sound recognition function 320 running in the response message generation module 210 detects a response utterance, the process proceeds to Step 5 and the sound information in the response utterance is compared to the sound information in one or more instances of a training utterance stored in the training sound store 330 described earlier with reference to FIG. 4. However, if in Step 4 no response to the played alert message is detected after a time out period, then the FOB response message generator 310 can generate and send a message to the ENS 200 that either does not have a response code, or has a response code indicating the no response to the played alert message is detected. If the comparison performed in Step 5 results in a match, then the process proceeds to Step 9 in FIG. 8B and the response code associated with the matching instance of a training sound is placed into a response message format and transmitted by the FOB to the ENS. If in Step 7, the logic determines that the comparison performed in Step 5 does not result in a match, then in the process proceeds to Step 8 and the message generator 310 generates and sends a response message to the ENS that does not include a response code, or optionally includes a response code that indicates that some response to the alert message was detected, but that the response did not match any train sound instance.

The forgoing description, for purposes of explanation, used specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

I claim:

1. In an event notification system, a method of training a mobile communication device, comprising:

entering, by a mobile communication device user, a response code that is associated with an alert training message;

controlling the mobile communication device to play the alert training message;

responding, by the mobile communication device user, to the played alert training message with an alert training message response utterance that is detected and stored by the mobile communication device in association with the response code;

receiving at the mobile communication device from the event notification system an alert message, and playing the alert message;

detecting, by the mobile communication device an alert message response utterance generated by the mobile communication device user, and matching the detected alert message response utterance to the stored alert training message response utterance; and generating an alert response message having the response code that is associated with the alert training message, and transmitting the alert response message with the response code to the event notification system.

2. The method of claim 1, further comprising receiving at the event notification system the alert response message, detecting the response code and determining that the response code corresponds to a particular type of response by the mobile communication device user to the alert message, and based upon the type of response determining whether to initiate an action.

3. The method of claim 2, wherein the action is any one or more of cancelling an alert, delaying an alert, sending a message indicating that a task is complete, or requesting supervisory involvement.

4. The method of claim 1, wherein the mobile communication device maintains instructions for entering response codes that are associated with the alert training message.

5. The method of claim 4, wherein the instructions can be played by the mobile communication device in a text format or an audio format.

6. The method of claim 1, wherein the mobile communication device can be placed into a training mode by the user.

7. The method of claim 6, wherein the user can place the mobile communication device into the training mode with either a verbal command or a manual command.

8. The method or claim 1, wherein the utterance corresponding to the alert message response is one or more spoken words, a pattern of audible or inaudible sounds all of which are not words, or a pattern of audible or inaudible sounds that are a combination of words and audible or inaudible sounds.

9. The method of claim 1, wherein the response code is a numeric value, an alphanumeric value or an alphabet character.

10. The method of claim 1, wherein the mobile communication device is configured to support two-way voice communication.

11. An alert message response system, comprising:

an event notification system connected over a wireless network with a mobile communication device that is trained to associate a training response sound, selectively uttered by a user of the mobile communication device in response to an alert training message, with a response code, and the mobile communication device operating to detect that a sound uttered by the mobile communication device user in response to an alert message received from the event notification system is the same as the training response sound, and generating and sending to the event notification system an alert response message having the response code; and the event notification system receiving the response message from the mobile communication device and using the response code to determine an action to take.

12. The system of claim 11, wherein the mobile communication device is trained by assigning a different response code to each one of a plurality of training sounds.

13. The system of claim 12, wherein the plurality of training sounds are stored in association with the mobile communication device.

14. The system of claim 13, wherein any one of the plurality of the training sounds can be selected to be played on the mobile communication device.

15. The system of claim 11, wherein the mobile communication device can be placed into a training mode by the mobile communication device user.

16. The system of claim 15, wherein the mobile communication device user can place the mobile communication device into the training mode with either a verbal command or a manual command.

17. The system of claim 11, wherein the utterance is one or more spoken words, a pattern of audible or inaudible sounds all of which are not words, or a pattern of audible or inaudible sounds that are a combination of words and audible or inaudible sounds.

18. The system of claim 11, wherein the response code is a numeric value, an alphanumeric value or an alphabet character.

19. The system of claim 11, wherein the action is any one or more of cancelling an alert, delaying an alert, sending a message indicating that a task is complete, or requesting supervisory involvement.

* * * * *